United States Patent
Piron et al.

(10) Patent No.: US 9,799,114 B2
(45) Date of Patent: Oct. 24, 2017

(54) METHOD, SYSTEM AND APPARATUS FOR QUANTITATIVE SURGICAL IMAGE REGISTRATION

(71) Applicants: Cameron Anthony Piron, Toronto (CA); Murugathas Yuwaraj, Toronto (CA)

(72) Inventors: Cameron Anthony Piron, Toronto (CA); Murugathas Yuwaraj, Toronto (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 0 days.

(21) Appl. No.: 15/514,111

(22) PCT Filed: Nov. 27, 2014

(86) PCT No.: PCT/CA2014/000849
§ 371 (c)(1),
(2) Date: Mar. 24, 2017

(87) PCT Pub. No.: WO2016/082017
PCT Pub. Date: Jun. 2, 2016

(65) Prior Publication Data
US 2017/0249737 A1    Aug. 31, 2017

(51) Int. Cl.
*G06T 7/00* (2017.01)
*A61B 34/10* (2016.01)
(Continued)

(52) U.S. Cl.
CPC .......... *G06T 7/0012* (2013.01); *A61B 5/0035* (2013.01); *A61B 5/0066* (2013.01);
(Continued)

(58) Field of Classification Search
CPC ..... G06T 7/0012; A61B 34/10; G61B 5/0035; G61B 5/0066; G61B 5/0075; G61B 5/055
See application file for complete search history.

(56) References Cited

U.S. PATENT DOCUMENTS 6,109,270 A * 8/2000 Mah .................... A61B 5/7264
128/924
2003/0053697 A1   3/2003 Aylward et al.
(Continued)

FOREIGN PATENT DOCUMENTS

WO    2014127321 A2    8/2014

OTHER PUBLICATIONS

International Preliminary Report on Patentability dated Jan. 27, 2017 for PCT International Application No. PCT/CA2014/000849.
(Continued)

*Primary Examiner* — Kim Vu
*Assistant Examiner* — Molly Delaney
(74) *Attorney, Agent, or Firm* — Kristjan Spence; Perry + Currier Inc.

(57) ABSTRACT

A method in a computing device for quantitative surgical image registration includes: prior to a surgical procedure, obtaining, using a first imaging modality, a preoperative image of patient tissue and a plurality of preoperative measurements of a material property of the patient tissue. The preoperative measurements correspond to respective points in the preoperative image. The method includes storing the preoperative image and the preoperative measurements, and during the surgical procedure, using a second imaging modality, capturing an intraoperative image of the patient tissue and a second plurality of intraoperative measurements of the material property of the patient tissue. The intraoperative measurements correspond to respective points in the intraoperative image. The method includes comparing
(Continued)

the first and second pluralities of measurements to determine a transformation for registering the preoperative image and the intraoperative image; and storing the transformation in association with one of the intraoperative image and the preoperative image.

20 Claims, 8 Drawing Sheets

(51) Int. Cl.
    *A61B 5/00*     (2006.01)
    *A61B 5/055*     (2006.01)
    *A61B 6/03*     (2006.01)
    *A61B 8/08*     (2006.01)
    *A61B 6/00*     (2006.01)

(52) U.S. Cl.
    CPC ............ *A61B 5/0075* (2013.01); *A61B 5/055* (2013.01); *A61B 6/032* (2013.01); *A61B 6/5247* (2013.01); *A61B 8/5261* (2013.01); *A61B 34/10* (2016.02); *A61B 2505/05* (2013.01); *G06T 2207/10081* (2013.01); *G06T 2207/10088* (2013.01); *G06T 2207/10101* (2013.01); *G06T 2207/30016* (2013.01); *G06T 2207/30101* (2013.01)

(56) References Cited

U.S. PATENT DOCUMENTS

| | | |
|---|---|---|
| 2007/0019846 A1 | 1/2007 | Bullitt et al. |
| 2008/0319308 A1* | 12/2008 | Tang ...................... A61B 5/055 600/416 |
| 2009/0306581 A1 | 12/2009 | Claus |
| 2011/0206291 A1 | 8/2011 | Kashani et al. |
| 2012/0069298 A1* | 3/2012 | Ng ....................... A61B 3/0025 351/206 |
| 2012/0188352 A1 | 7/2012 | Wittenberg et al. |
| 2013/0094745 A1 | 4/2013 | Sundar |
| 2013/0195338 A1 | 8/2013 | Xu et al. |
| 2017/0231499 A1* | 8/2017 | Gimzewski .......... A61B 5/0048 |

OTHER PUBLICATIONS

International Search Report dated Aug. 12, 2015 for International Patent Application No. PCT/CA2014/000849.

Written Opinion dated Aug. 12, 2015 for International Patent Application No. PCT/CA2014/000849.

Lennart Henning Stieglitz et al., "The Silent Loss of Neuronavigation Accuracy: A Systematic Retrospective Analysis of Factors Influencing the Mismatch of Frameless Stereotactic Systems in Cranial Neurosurgery", published online Jan. 17, 2013, Congress of Neurological Surgeons, www.neurosurgery-online.com, Neurosurgery 72:796-807, 2013.

Petter Risholm et al.:, "Multi-Modal Image Registration for Pre-Operative planning and Image Guided Neurosurgical Procedures", published online Apr. 22, 2011, Neurosurg Clin N Am. Apr. 2011; 22(2): 197-206. doi: 10.1016/j.nec.2010.12.001.

Examination Report dated Apr. 28, 2017 for Canadian Patent Application No. 2959209.

* cited by examiner

METHOD, SYSTEM AND APPARATUS FOR QUANTITATIVE SURGICAL IMAGE REGISTRATION

FIELD

The specification relates generally to medical imaging, and specifically to a method, system and apparatus for quantitative surgical image registration.

BACKGROUND

In medical imaging, image registration (the alignment of two images with each other such that both are placed in a common coordinate system) generally requires the identification of features in each image, such as edges, bright spots and the like. Having identified such features, image registration algorithms attempt to match similar features between the images. However, different images may have widely varying contrasts, colour schemes and the like, complicating feature identification. This may be especially true when attempting to register images taken with different modalities (e.g. MRI and ultrasound).

Current image registration techniques may therefore result in inaccurate registration, particularly in medical applications, and may also impose onerous computational burdens.

SUMMARY

According to an aspect of the specification, a method of image registration is provided, comprising: prior to a surgical procedure, obtaining a preoperative image of patient tissue at a computing device using a first imaging modality; using the first imaging modality, obtaining a first plurality of preoperative measurements of a material property of the patient tissue at the computing device, the preoperative measurements corresponding to respective points in the preoperative image; storing the preoperative image and the preoperative measurements in a memory of the computing device; during the surgical procedure, obtaining an intraoperative image of the patient tissue at the computing device using a second imaging modality; using the second imaging modality, obtaining a second plurality of intraoperative measurements of the material property of the patient tissue at the computing device, the intraoperative measurements corresponding to respective points in the intraoperative image; comparing the first and second pluralities of measurements at the computing device to determine a transformation for registering the preoperative image and the intraoperative image; and storing the transformation in the memory in association with one of the intraoperative image and the preoperative image.

According to another aspect of the specification, a computing device is provided, comprising: a memory; a processor interconnected with the memory, the processor configured to: prior to a surgical procedure, obtain a preoperative image of patient tissue using a first imaging modality; using the first imaging modality, obtain a first plurality of preoperative measurements of a material property of the patient tissue at the computing device, the preoperative measurements corresponding to respective points in the preoperative image; store the preoperative image and the preoperative measurements in the memory; during the surgical procedure, obtain an intraoperative image of the patient tissue using a second imaging modality; using the second imaging modality, obtain a second plurality of intraoperative measurements of the material property of the patient tissue, the intraoperative measurements corresponding to respective points in the intraoperative image; compare the first and second pluralities of measurements to determine a transformation for registering the preoperative image and the intraoperative image; and store the transformation in the memory in association with one of the intraoperative image and the preoperative image.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
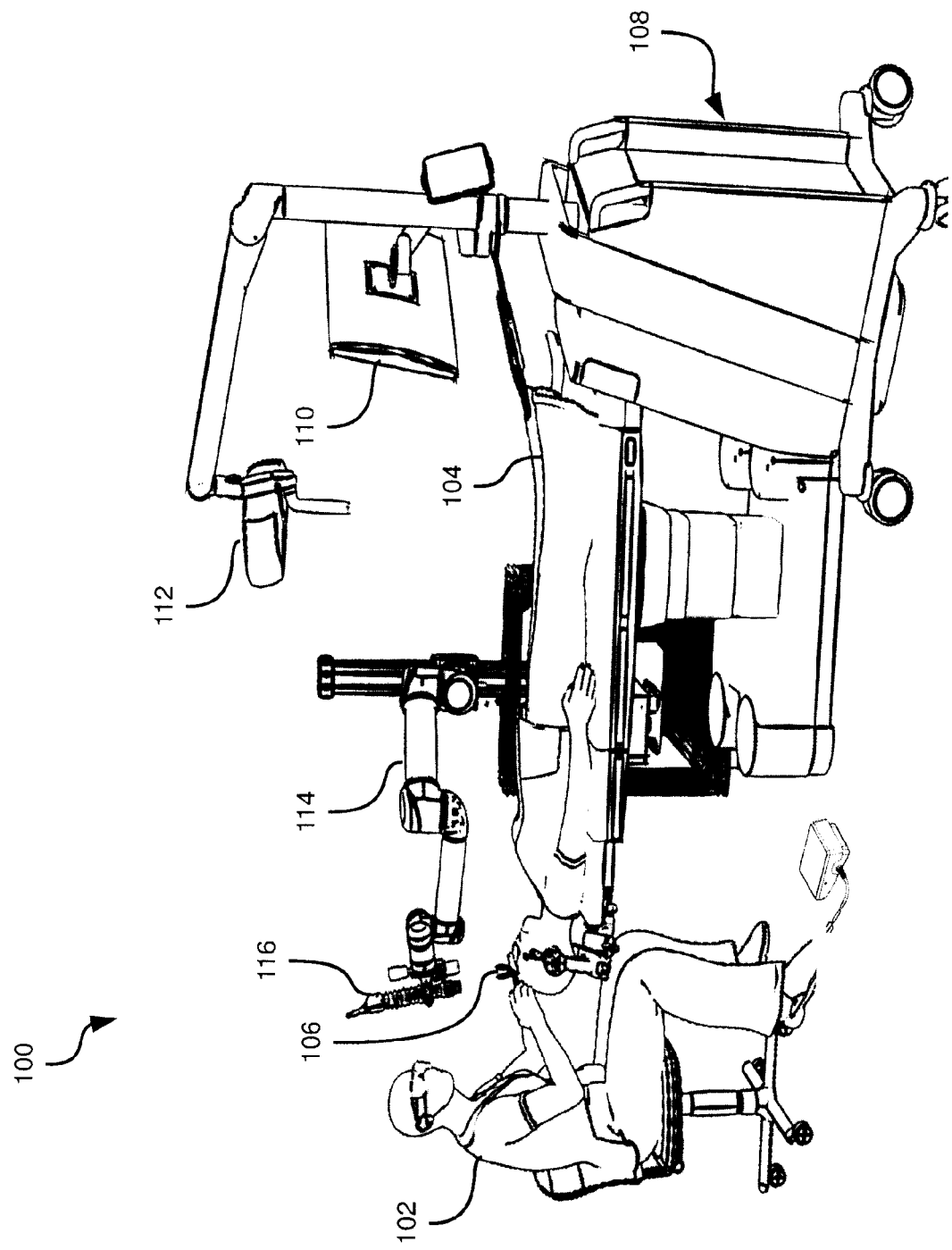
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 102, any of the above-mentioned surgical tools, or any combination thereof. Such markers, also referred to as fiducial markers, may also be mounted on patient 104, for example at various points on patient 104's head. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 102 by robotic arm 114, and may capture images of the brain of patient 104 for presentation on display 110. The movement of robotic arm 114 to place external scope 116 correctly over access port 102 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of patient 104's brain. Such preoperative images may be collected using any of a variety of imaging modalities, such as Magnetic Resonance Imaging (MRI), Optical Coherence Tomography (OCT), ultrasound, Computed Tomography (CT), optical spectroscopy and the like. Such preoperative images may be used for planning purposes. During the procedure, additional images may be collected of patient 104's brain, using any of the above-mentioned modalities. Further, the intraoperative images may be acquired with modalities having different resolutions than those used preoperatively. For example, an intraoperative ultrasound may provide data at a higher resolution over a smaller area by inserting an ultrasound probe within the brain of patient 104 than an external ultrasound could provide before the surgical procedure. As will be described in further detail below, the computing device housed in equipment tower 108 can perform various actions to register preoperative images with intraoperative images (that is, place both types of image in a common coordinate system), allowing the data obtained before the surgical procedure to be combined and presented simultaneously on display 110.

Figure 2:
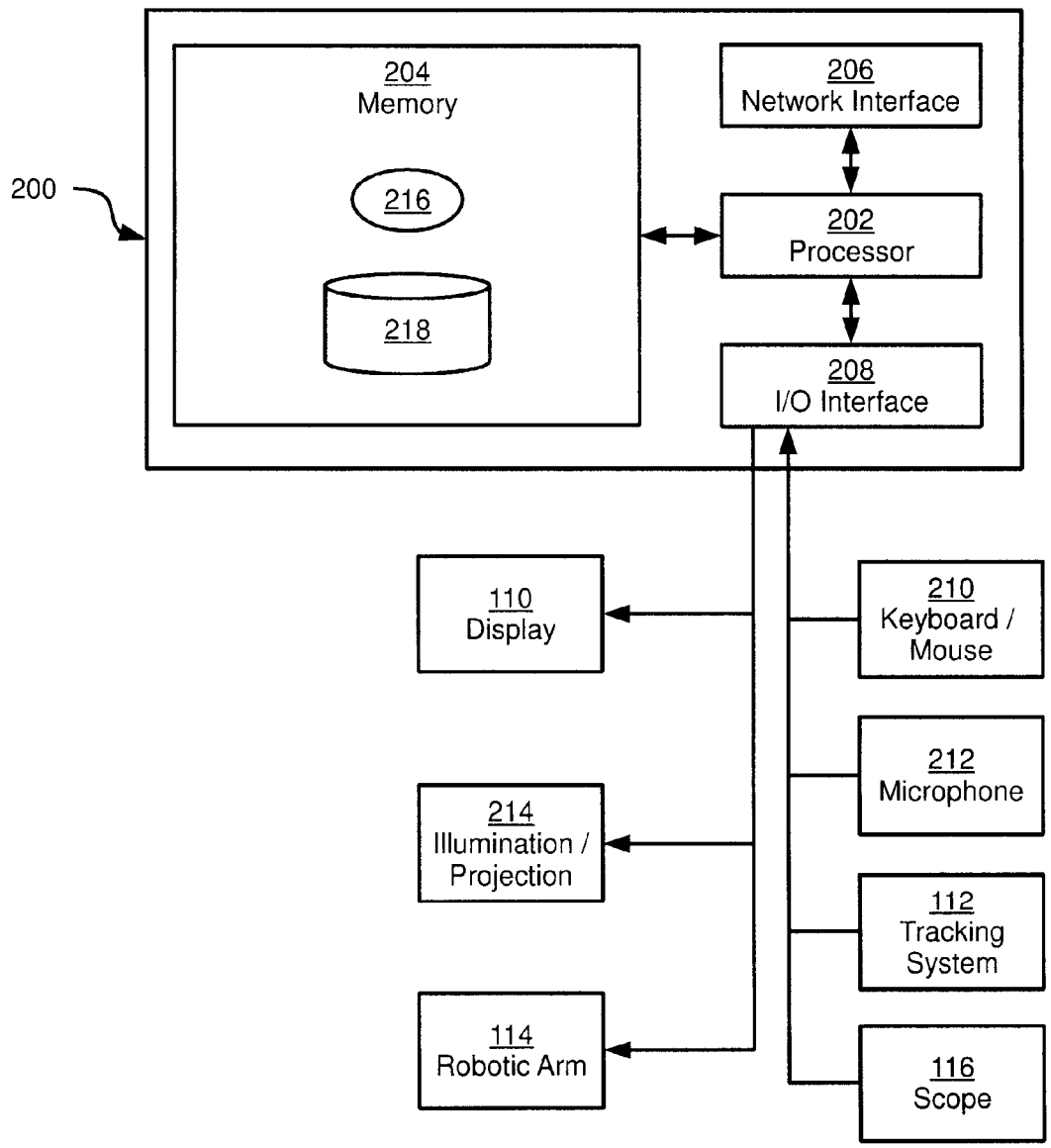
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 200. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, an image registration application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as image data relating to patient 104, such as MRI and CT scans, three-dimensional models of the brain of patient 104, and the like.

As mentioned above, computing device 200 is configured, via the execution of application 216 by processor 202, to perform various functions related to registering preoperatively-acquired images of patient 104 with intraoperatively-acquired images. Those functions will be described in further detail below.

Figure 3:
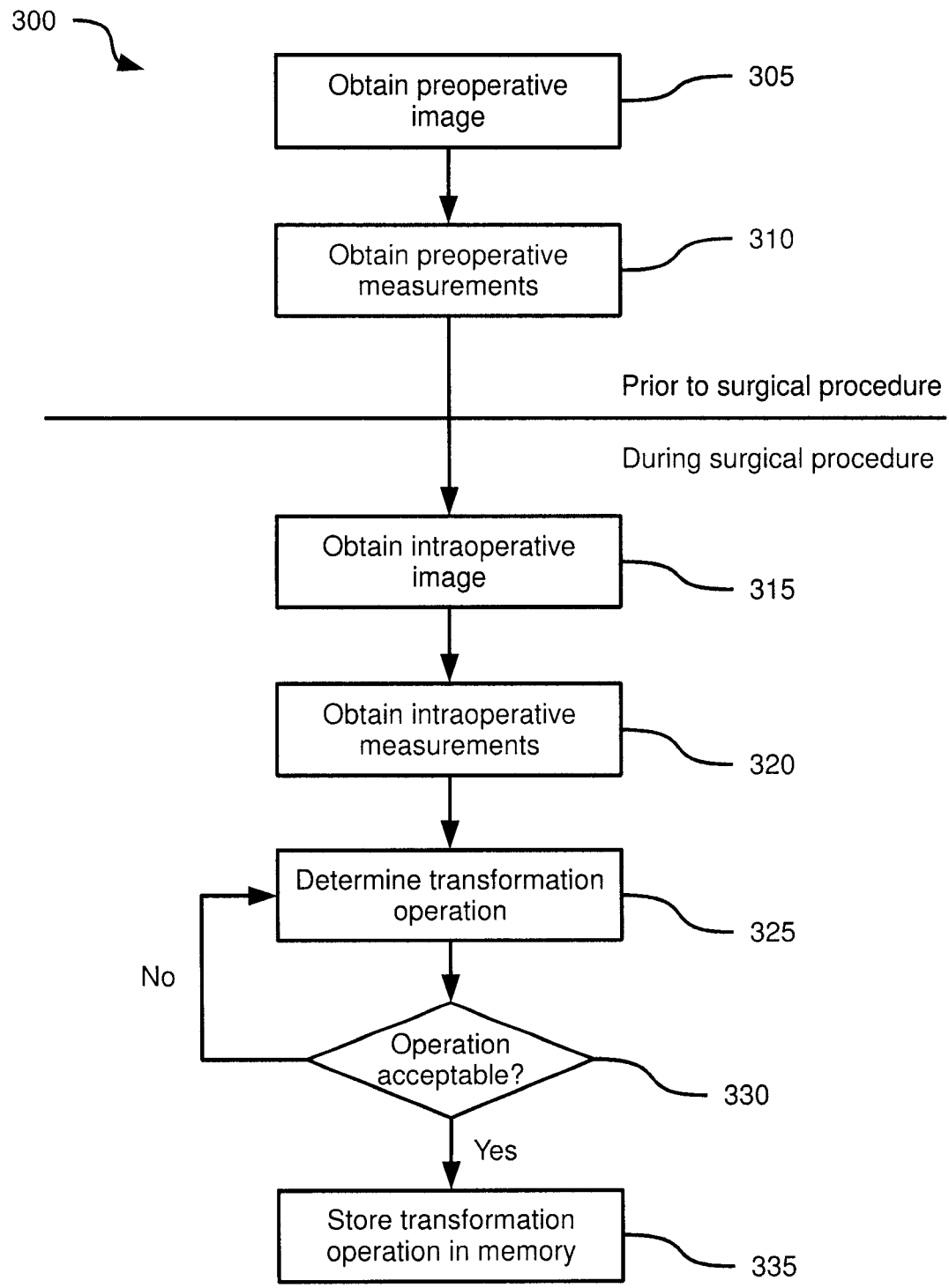
FIG. 3 depicts a method of image registration, according to a non-limiting embodiment.

Referring now to FIG. 3, a method 300 of registering images is depicted. Method 300 will be discussed in conjunction with its performance on computing device 200 as deployed in operating theatre 100. It will be apparent to those skilled in the art, however, that method 300 can also be implemented on other computing devices in other systems.

Figure 4:
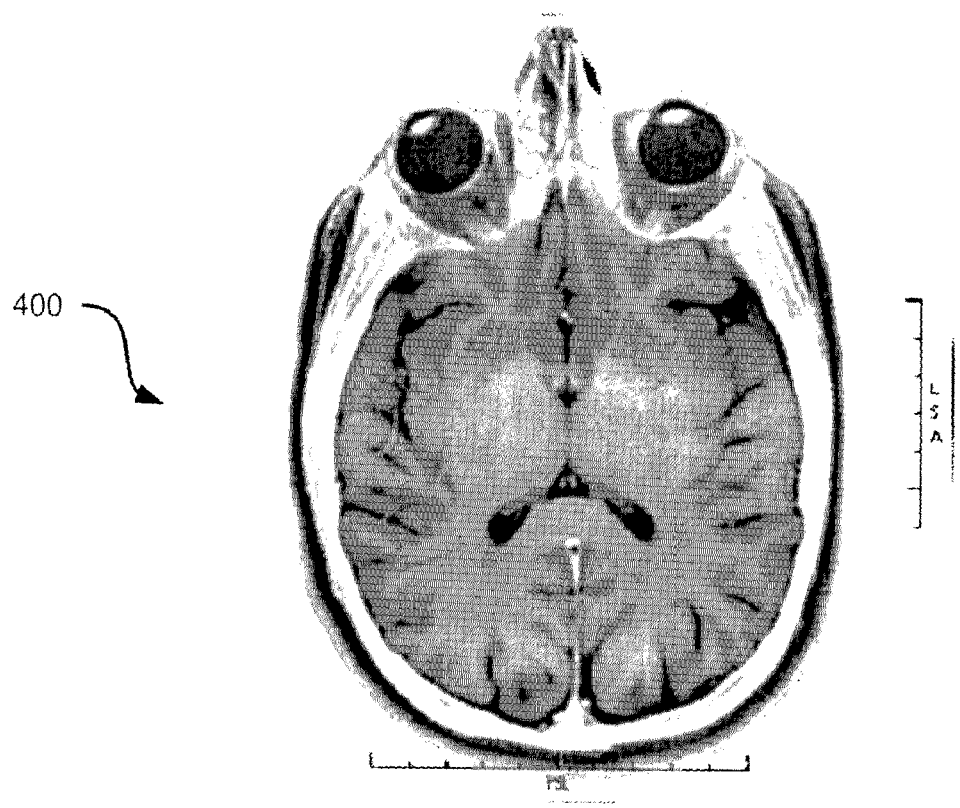
FIG. 4 depicts an example preoperative image, according to a non-limiting embodiment.

At block 305, computing device 200 is configured to obtain a preoperative image of at least a portion of patient 104, using a first imaging modality. For example, the preoperative image may be an MRI scan, an example of which is shown in FIG. 4. It is contemplated that the preoperative image captured at block 305 may be two-dimensional or three-dimensional. Further, the method of acquisition of the preoperative image is not particularly limited. For example, computing device 200 may be connected directly to an MRI scanner (not shown), and receive data from the MRI scanner during the scan. In other examples, computing device 200 may receive the preoperative image from another computing device via network interface 206. The preoperative image is stored in memory 204, particularly in patient data repository 218. The preoperative image can contain or be associated with data describing the physical size of the area of patient 104 that was imaged. Such data can appear in the form of a resolution, dimensions, and the like.

At block 310, computing device 200 is configured to obtain a first plurality of preoperative measurements of a material property of the above-mentioned portion of patient 104, acquired using the same imaging modality as in block 305. The preoperative measurements correspond to respective points in the preoperative image. The preoperative measurements can be obtained in a variety of ways. In some examples, the preoperative measurements can be derived from the preoperative image itself. In such examples, the preoperative image may be taken using a known imaging method, such as MRI elastography, in which vibration is applied to the tissue of patient 104 during an MRI scan. The resulting image (obtained at block 305) may therefore be a visual representation of the stiffness of the imaged tissue. However, the absolute values of the pixels (or voxels, in a three-dimension image) may not convey the actual stiffness of the imaged tissue. Thus, at block 310, computing device 200 may be configured to derive absolute measures of stiffness from the preoperative image, using previously obtained calibration data for the imaging apparatus (e.g. the MRI scanner). The mathematical basis for deriving measurements such as tissue stiffness from MRI elastography scans and other imaging methods is known to those skilled in the art. In brief, elastograms can be computed from strain profiles obtained through measurement, given various assumptions based on tissue properties and applied stresses.

In other embodiments, the measurements obtained at block 310 can be obtained by computing device 200 from a source other than the preoperative image. For example, computing device 200 may be configured, shortly before or shortly after obtaining the preoperative image at block 305 ("shortly" being a timeframe selected to minimize or eliminate movement of the patient tissue during the timeframe), to obtain a separate scan, using the same imaging modality as in block 305, and to derive the measurements from that separate scan.

The preoperative measurements can be stored in memory 204 (e.g. in patient data repository 218) in association with the preoperative image. For example, referring to FIG. 5, preoperative image 400 is shown, along with preoperative measurements arranged in a matrix 500 corresponding to the pixels (or voxels, as mentioned previously) of image 400. In other words, the preoperative measurements can be stored with indications of which point in image 400 each measurement corresponds to. The specific implementation of such storage is not particularly limited. In some embodiments, for example, the measurements may be added to fields in each pixel or voxel of image 400 itself Having obtained the preoperative image and the preoperative measurements at blocks 305 and 310, computing device 200 is configured to proceed to block 315 of method 300. As illustrated in FIG. 3, blocks 315-330 of method 300 take place during the surgical procedure, whereas blocks 305-310 took place prior to the surgical procedure. As will now be apparent to those skilled in the art, certain imaging modalities may only be available preoperatively (e.g. high-field MRI), while other modalities may only be available intraoperatively (e.g. Doppler ultrasound). Certain image modalities may only be available intraoperatively because they require direct access to tissue (e.g. brain, spine, skeletal joints and the like), via openings such as a craniotomy or access port 106. Preoperative imaging does not provide such direct access, and therefore the imaging modalities available preoperatively may be limited.

Figure 6:
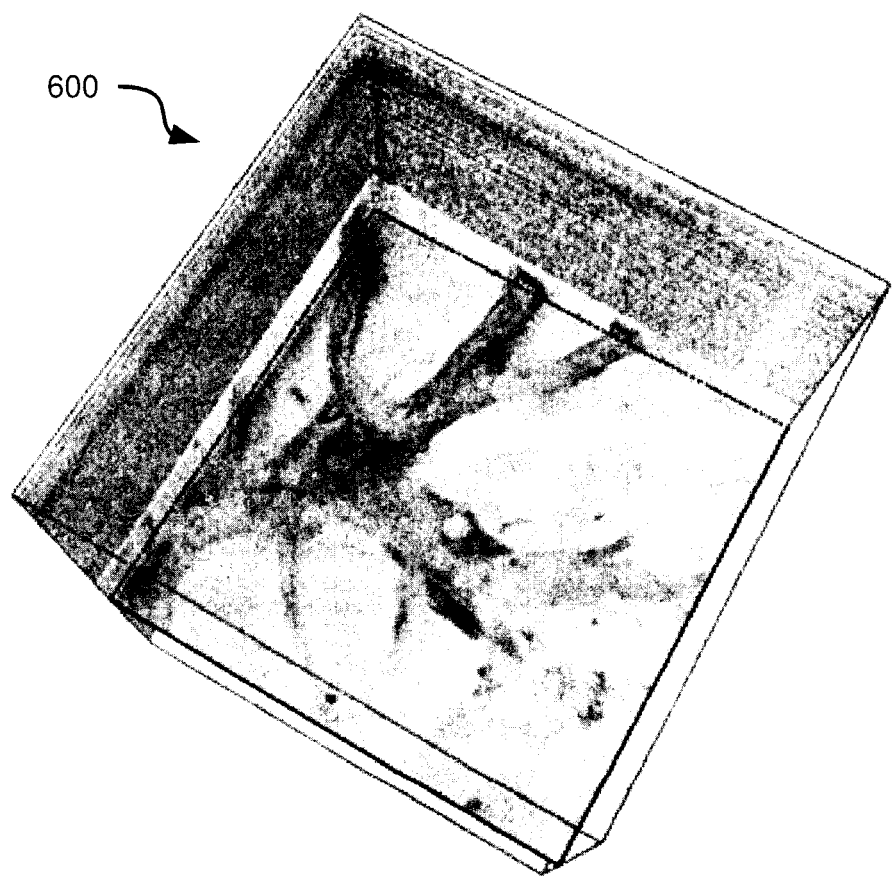
FIG. 6 depicts an example intraoperative image, according to a non-limiting embodiment.

At block 315, during the surgical procedure computing device 200 is configured to obtain an intraoperative image using a second imaging modality that is different from the first imaging modality used at block 305. Thus, if MRI is used at block 305, block 315 may involve the use of ultrasound, optical spectroscopy, low field intraoperative MRI (iMRI) or the like. An example of an intraoperatively-obtained image 600 is shown in FIG. 6. Image 600 was captured using OCT as the second imaging modality. With the exceptions of the timing of acquisition and the different imaging modality, the obtaining of an intraoperative image at block 315 is as described above in connection with block 305. The intraoperative image can be stored in patient data repository 218, and can also contain or be associated with data describing the physical size and position of the area of patient 104 that was imaged. Such data can appear in the form of a resolution, dimensions, and the like.

Next, at block 320, computing device 200 is configured to obtain a second plurality of intraoperative measurements of a material property at block 310 of the above-mentioned portion of patient 104. Of particular note, the measurements obtained at block 320 are measurements of the same material property measured at block 310. Thus, if preoperative measurements of fluid flow in mm/s were obtained at block 310, then for the same performance of method 300, at block 320 the intraoperative measurements are of fluid flow also in mm/s. These intraoperative measurements may be derived from the intraoperative image obtained at block 315, or they may be obtained in a separate scan, as mentioned in connection with block 310.

It will now be apparent that not all combinations of two imaging modalities can be used to derive the same physical measurements of material properties. Thus, the selection of the first imaging modality for the preoperative image and measurements constrains the available imaging modalities for the intraoperative image and measurements. The table below summarizes the available combinations of imaging modalities, and the measurements such combinations are capable of obtaining.

TABLE 1

Compatible Imaging Modalities and Measurements

| Modality | Material Property | | | |
|---|---|---|---|---|
| | Flow (mm/s) | Stiffness (N/mm$^2$) | Anisotropy | Metabolite concentration |
| MRI | Phase-contrast MRI | MRI Elastography | Fractional Anisotropy Map | MRI Spectroscopy OR Delta Relaxometry MRI |
| OCT | Doppler-flow/ Phase-contrast | OCT Elastography | Polarization Sensitive OCT | N/A |
| Ultrasound | Doppler-flow | Ultrasound Elastography | Spectral analysis of ultrasound backscatter | N/A |
| CT | Phase-contrast Angiography | N/A | N/A | N/A |
| Optical Spectroscopy | N/A | N/A | N/A | Raman Spectroscopy |

More specifically, each cell in Table 1 identifies the imaging method to be used to measure the relevant material property using the relevant imaging modality. For example, in order to obtain measurements of flow using MRI as an imaging modality, the imaging method of phase contrast MRI can be used. To obtain measurements of flow using CT, on the other hand, phase contrast angiography can be used. As another example, during ultrasound imaging, the ultrasound backscatter signal can be measured for different orientations of transmitted ultrasound waves relative to the tissue. The backscatter measurements can be correlated to tissue anisotropy. As seen in Table 1, anisotropy measurements (that is, measurements of how directionally restricted fluid flow is in a tissue) can also be obtained through the use of MRI to generate a fractional anisotropy map, also referred to as tractography data (data depicting fluid flow tracts, which indicate structural properties such as nerve bundles). This technique is also referred to as diffusion tensor imaging (DTI). Anisotropy measurements can further be obtained through the use of OCT, in particular by employing polarization-sensitive OCT (PS-OCT) to measure tissue anisotropy. The technique of measuring anisotropy with PS-OCT may also be referred to as optical diffusion tensor imaging (ODTI). Thus, anisotropy measurements obtained preoperatively using MRI (specifically, MRI-based DTI) can be registered to anisotropy measurements obtained intraoperatively using OCT (specifically, polarization-sensitive OCT) during the performance of method 300.

It will also be apparent to those skilled in the art, from Table 1, that some imaging modalities are not currently combinable in method 300. For example, if the preoperative image and measurements of stiffness are obtained using MRI as the first imaging modality, then blocks 315-320 cannot be performed using optical spectroscopy as the second imaging modality, as optical spectroscopy presently does not allow the measurement of tissue stiffness. More generally, cells containing "N/A" identify imaging modalities that are not presently capable of measuring the corresponding material property. It is contemplated, however, that additional techniques may be developed to measure those material properties with previously incompatible imaging modalities; any newly developed measuring techniques would be amenable to use in method 300.

Figure 5:
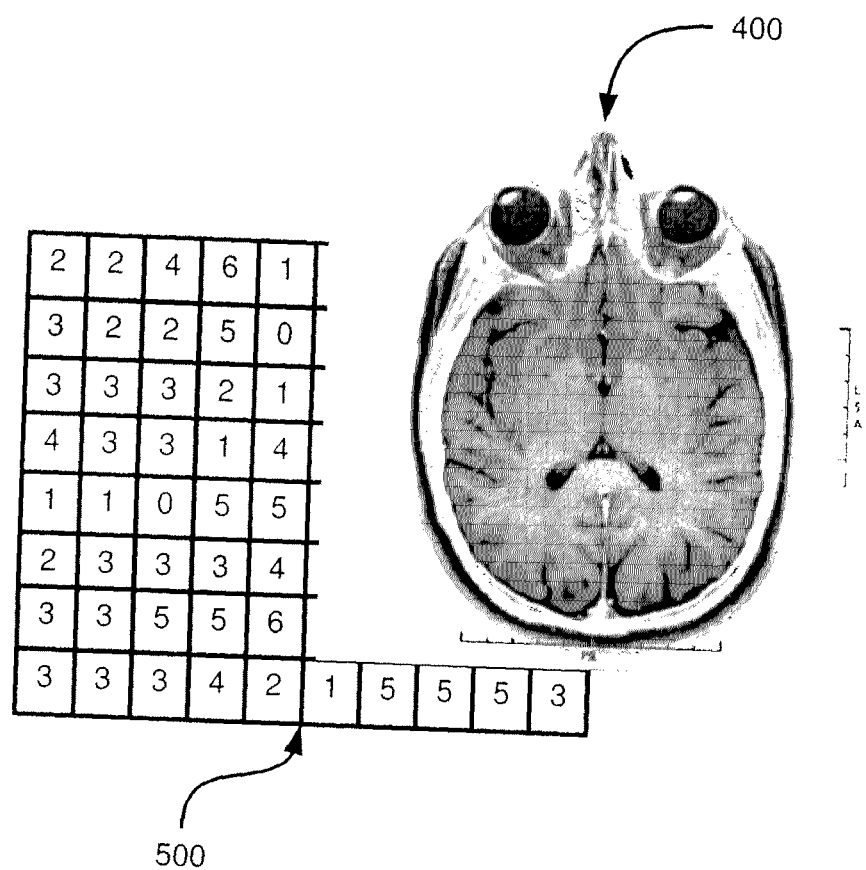
FIG. 5 depicts an example of preoperative material property measurements associated with the preoperative image of FIG. 4, according to a non-limiting embodiment.

The intraoperative measurements of the material property can be stored in memory 204 in conjunction with the intraoperative image, as described above in connection with the preoperative measurements and FIG. 5.

Responsive to obtaining the intraoperative image and intraoperative measurements, at block 325 computing device 200 is configured to register the intraoperative image obtained at block 315 with the preoperative image obtained at block 305. Image registration refers to the process of placing both images in a common coordinate system, such that any given set of coordinates in the common system identifies portions of both images depicting the same area of patient 104. In general, each obtained image begins with an image-specific coordinate system. For example, a two-dimensional preoperative image may have a coordinate system in which the origin lies at the lower-left corner of the image. A two-dimensional intraoperative image may also have a coordinate system in which the origin lies at the lower-left corner of the image. However, because the two images may not depict exactly the same area of patient 104, and because the different imaging modalities used to obtain the images may have different resolutions, the two coordinate systems cannot be directly compared. That is, the pixel located at (1200, 205) in the preoperative image may depict an entirely different portion of patient 104 than the pixel at (1200, 205) in the intraoperative image.

Therefore, in order to align the preoperative image and the intraoperative image on a common coordinate system, a transformation operation is applied to one of the images. In the present example, it is contemplated that the transformation operation is to be applied to the intraoperative image, but the transformation operation can also be applied to the preoperative image. The nature of the transformation is not particularly limited, and a variety of algorithms will occur to those skilled in the art for determining such transformation operations. In general, the transformation operation manipulates the pixels or voxels of one or both of the images (e.g. by translation, rotation, distortion, scaling, and the like) to place the pixels or voxels in the common coordinate system.

Figure 7A:
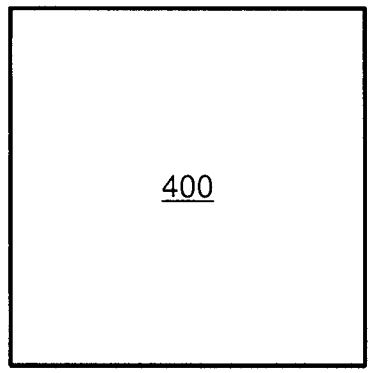
FIGS. 7A and 7B depict the transformation of the intraoperative image of FIG. 6, according to a non-limiting embodiment.
Figure 7A:
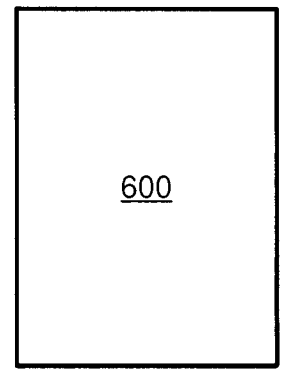
Figure 7B:
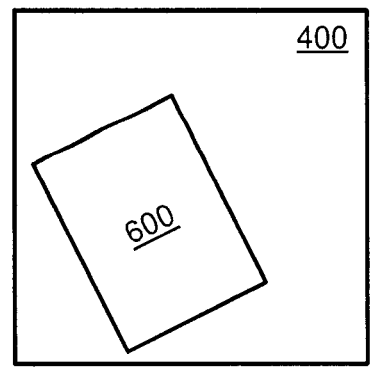

An example of such transformation is shown in FIGS. 7A and 7B. In particular, preoperative image 400 and intraoperative image 600 are shown in FIG. 7A in their original states. Following image registration, in FIG. 7B, images 400 and 600 are shown aligned such that any given set of coordinates refers to the same portion of patient 104 regardless of which of the two images one refers to. As a result, as will be discussed below in greater detail, image 400 and image 600 can be overlaid or combined to generate a composite image of an area of patient 104.

Of particular note, to perform the determination at block 325, computing device 200 is configured to compare not the preoperative and intraoperative images themselves, but instead to compare the preoperative measurements with the intraoperative measurements. The underlying assumption behind the determination at block 325 is that any given area of patient 104 will have closely matching material property measurements both before and during the medical procedure, and that matching preoperative measurements with intraoperative measurements will therefore effectively align the associated preoperative and intraoperative images relative to patient 104.

Computing device 200 can therefore be configured to automatically optimize various transformation parameters, such as translation, scaling and rotation, by computing a cost function reflecting the overall difference, or error, between the preoperative measurements and the intraoperative measurements. Such optimizations may be performed using a variety of conventional algorithms (e.g. algorithms that maximize mutual information, such as quasi-Newton, simultaneous perturbation and the like). Computing device 200 can be configured to select the set of transformation parameters yielding the lowest cost function, indicating that the selected set of transformation parameters provides the closest match between the preoperative measurements and the intraoperative measurements. A close match in turn indicates that the matching measurements were likely obtained from the same portion of patient 104.

It is contemplated that additional transformation parameters beyond those mentioned above may be selected by computing device 200. For example, while translation, scaling and rotation are referred to as linear or rigid transformations, further transformation parameters allow for non-rigid transformations, which can warp some regions within an image without warping others, or while warping other regions in different ways.

Having determined a transformation operation, computing device 200 can be configured to determine whether the transformation operation is acceptable at block 330. The determination at block 330 is optional, and may be omitted in some embodiments. The determination at block 330 can take a variety of forms. For example, computing device 200 may store in memory 204 a threshold, and in order to be acceptable the transformation operation must result in an overall error between the registered images that falls below the threshold. Thus, at block 330, computing device 200 may retrieve the threshold, and determine whether the above-mentioned cost function for the selected transformation parameters yields a result that is smaller than the threshold.

In other embodiments, at block 330 computing device 200 may await input, for example from keyboard/mouse 210, confirming or denying that the transformation operation is acceptable. Prior to receiving such input, computing device 200 can control display 110 to present an overlay of preoperative image 400 and intraoperative image 600, such as that shown in FIG. 7B. A medical professional such as surgeon 102 can then view the overlay and instruct computing device 200 whether then image registration is acceptable or not.

When the determination at block 330 is negative, computing device 200 can be configured to return to block 325 to attempt a further determination of a transformation operation. In other embodiments, computing device 200 may be configured instead to present an error message on display 110 and halt the performance of method 300.

When the determination at block 330 is affirmative, however, performance of method 300 proceeds to block 335, at which computing device 200 is configured to store the transformation operation determined at block 325 in memory 204 (e.g. in patient data repository 218 in association with preoperative image 400 and intraoperative image 600).

Following storage of the transformation operation, computing device 200 can take a variety of further actions, as will be discussed below. It is also contemplated that computing device 200 can repeat the performance of blocks 315-335 for additional intraoperative images, thus registering a plurality of intraoperative images to the preoperative image. For example, referring to Table 1, a preoperative MRI image may be registered with intraoperative OCT, ultrasound and CT images based on measurements of flow derived from each of those imaging modalities.

In another example performance of method 300, the preoperative image obtained at block 315 is obtained using the MRI modality, and the preoperative measurements are anisotropy measurements. In other words, the technique of DTI is employed at blocks 305 and 310, resulting in image 400 shown in FIG. 4. The pre-operative measurements obtained in this manner include anisotropy measurements for the patient's entire brain. Further, the intraoperative image and measurements obtained at blocks 315 and 320 are obtained using the OCT modality, and in particular polarization-sensitive OCT. Image 600 is an example of an intraoperative OCT image. Thus, the intraoperative measurements obtained at block 320 are also tissue anisotropy measurements. However, the intraoperative measurements in this example cover a smaller volume of patient 104 than the preoperative measurements. More specifically, the intraoperative measurements may be collected using a probe inserted into access port 106, and may therefore cover a disk-shaped region of patient 104's brain. The region may have various dimensions, but in general represents only a subset of the brain. For example, the intraoperative measurements may cover a disk-shaped region with a diameter of about 13 mm, centered on the tip of the probe at the bottom of access port 106, and a depth of 2-3 mm.

At blocks 325 and 330 in the above-mentioned example, therefore, the anisotropy measurements from block 310 are compared with the anisotropy measurements from block 320 to identify the location of image 600 within image 400 (that is, which portion of patient 104's brain is depicted by both images 400 and 600).

Figure 8:
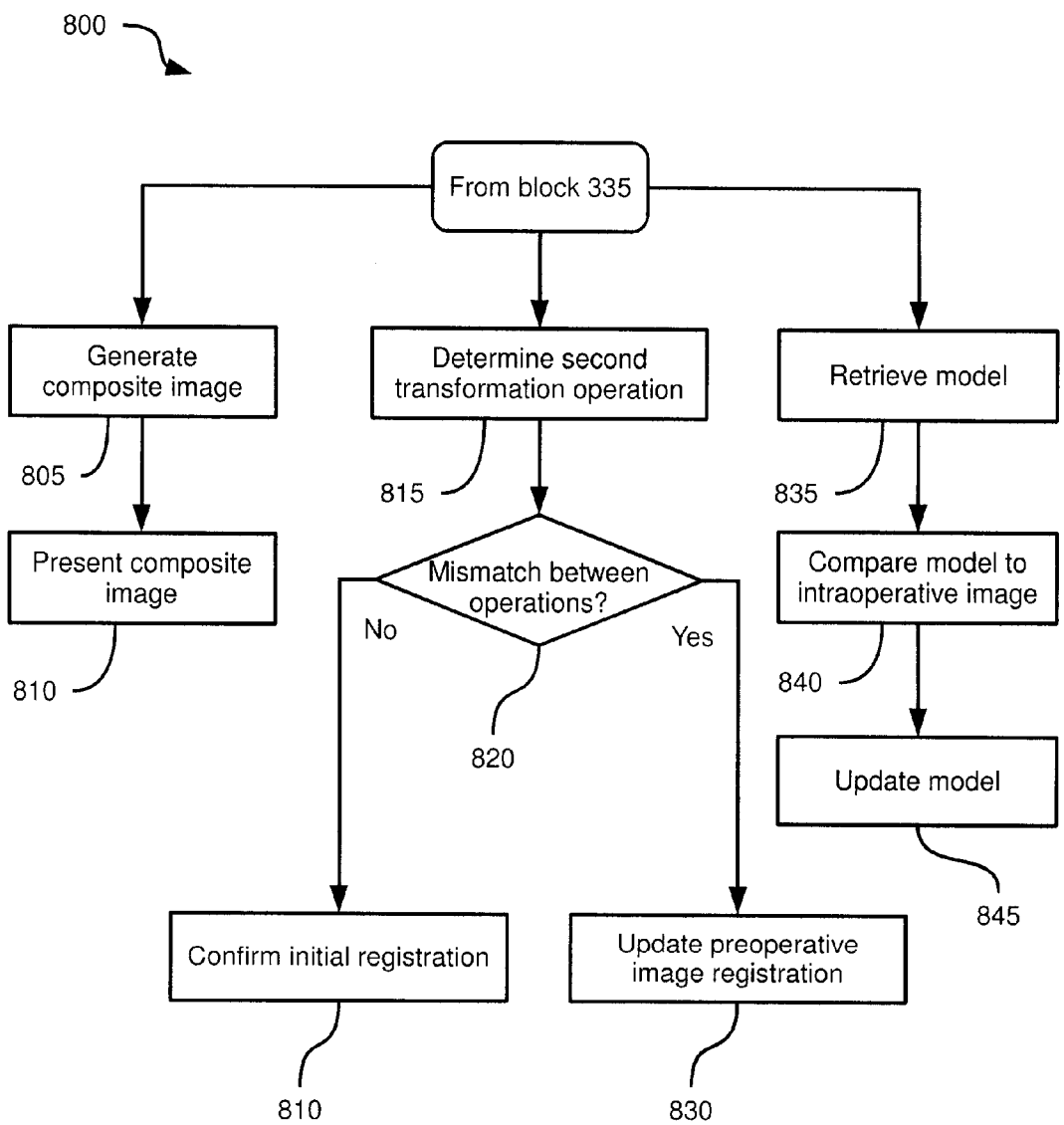
FIG. 8 depicts a method of presenting the transformed intraoperative image of FIG. 7B, according to a non-limiting embodiment.

Turning to FIG. 8, a method 800 of presenting the transformation operation determined through method 300 is depicted. Method 800 will be described in conjunction with its performance by computing device 200 intraoperatively. However, it is contemplated that method 800 can also be performed in other suitable systems. Note that method 800 includes three branches, each departing from block 335 of method 300. The three branches need not all be implemented in any given performance of method 800, although all three branches can be performed.

The first branch of method 800 begins at block 805, at which computing device 200 is configured to generate a composite image from preoperative image 400 and intraoperative image 600. More specifically, computing device 200 is configured to retrieve preoperative image 400 and intraoperative image 600 from memory 204, and to retrieve the transformation operation determined at block 325. Computing device 200 is then configured to apply the transformation operation to one or the other of the preoperative and intraoperative images (in the examples discussed above, the operation is applied to intraoperative image 600). Computing device 200 is then configured to generate a composite image by combining preoperative image 400 with the transformed version of intraoperative image 600.

Following generation of the composite image, computing device 200 is configured to present the composite image (see FIG. 7B, for example) on display 110. Computing device 200 may also store the composite image in memory 204.

The second branch of method 800, beginning at block 815, implements a method of confirming a registration of preoperative image 400 to patient 104. Prior to or at the start of a medical procedure, preoperative images may be transformed to place them in a common coordinate system with patient 104. Such transformation allows virtual models of surgical instruments to be overlaid on preoperative image 400 via the use of tracking system 112. During the medical procedure, however, the registration may become less accurate. For example, patient 104 or a portion of patient 104 (e.g. the brain) may shift, and as a result preoperative image 400 may no longer accurately map to the brain. With the results of method 300, computing device 200 can confirm the accuracy of the registration between preoperative image 400 and patient 104.

At block 815, computing device 200 is configured to determine a second transformation operation for intraoperative image 600 (the operation determined at block 325 being the "first"). The second transformation operation is determined using tracking system 112, and places intraoperative image 600 in a common coordinate system with patient 104, preoperative image 400 and any other tracked objects within operating theatre 100. It is assumed that the instrument used to obtain intraoperative image 600 (and the associated intraoperative measurements) bears a set of markers that are detectable by tracking system 112. Thus, tracking system 112 can determine the position and orientation of the imaging instrument within operating theatre 100, and determine a transformation operation to relocate the pixels or voxels of intraoperative image 600 from their local coordinates to a common coordinate system in operating theatre 100.

Having determined the second transformation operation, computing device 200 is configured to determine, at block 820, whether there is a mismatch between the transformation operation from block 325 and the transformation operation from block 815. In other words, two versions of intraoperative image 600 can be generated: one that has been registered to preoperative image 400 (which is, in turn, registered to patient 104), and another that has been registered directly to patient 104. If the registration of preoperative image 400 to patient 104 is accurate, then the two versions mentioned above should coincide closely. If, however, patient 104 has shifted, thus rendering the registration between preoperative image 400 and patient 104 inaccurate, then the two versions of intraoperative image 600 would be expected to diverge.

The nature of the determination at block 820 is not particularly limited. In some embodiments, computing device 200 may be configured to compare the two versions of intraoperative image 600 mentioned above, and generate an error estimate. If the error estimate rises above a predefined threshold, a mismatch is detected. In other embodiments, computing device 200 may be configured to compare the second version of intraoperative image 600, obtained at block 815, with preoperative image 400 and generate an error estimate. Again, if the error estimate rises above a predefined threshold, a mismatch is detected. In other embodiments, rather than the automatic methods mentioned above, computing device 200 may be configured to present preoperative image 400 on display 110, and to overlay the second version of intraoperative image 600 for visual comparison by a medical professional. Computing device 200 can then receive input (e.g. from keyboard/mouse 210) indicating whether there is a mismatch.

When the determination at block 820 is negative (that is, no mismatch exists), the performance of method 800 proceeds to block 825. At block 825, computing device 200 is configured to maintain the original registration of preoperative image 400 to patient 104. A message may be presented on display 110 confirming that the original registration remains accurate.

When the determination at block 820 is affirmative (that is, a mismatch exists), the performance of method 800 proceeds to block 830. At block 830, computing device 200 is configured to update the registration of preoperative image 400 to patient 104. This may be achieved by determining a transformation operation to register preoperative image 400 to the above-mentioned second version of intraoperative image 600 (using the second transformation operation). Updating of the registration may also be performed via receipt of input at computing device 200 from a medical professional such as surgeon 102. Such manual methods of registration will now occur to those skilled in the art.

The third branch of method 800 begins at block 835, and enables computing device 200 to update a preoperative model of patient 104 or a portion of patient 104 (such as the brain). Among the various planning activities that may precede a medical procedure, a model of patient 104's brain may be prepared. The model may, for example, predict one or more material properties at various points in the brain. An example of such modeling is described in Applicant's copending published patent application WO/2014/138997, titled "SYSTEM AND METHOD FOR DETECTING TISSUE AND FIBER TRACT DEFORMATION", the contents of which is hereby incorporated by reference. It is assumed in the present example performance of method 800 that the intraoperative measurements obtained at block 320 are measurements of the same material property as predicted in the model.

At block 835, computing device 200 can be configured to retrieve the above-mentioned model from memory 204. At block 840, computing device 200 can be configured to compare intraoperative image 600, as transformed by the operation from block 325, to the model. The comparison can include, for example, a generation of a error estimate between the model and intraoperative image 600. At block 845, computing device 200 can then be configured to update some or all of the model by replacing modeled values of the material property with values obtained from the intraoperative measurements.

From the above disclosure, various advantages may occur to those skilled in the art. For example, employing quantitative measurements of material properties rather than image-specific values (such as the brightness or colour of a pixel) may allow for more accurate registration of images, because the preoperative and intraoperative measurements, although gathered using different modalities, have the material property in common and are therefore more amenable to direct comparison. In addition, the above methods may facilitate the simultaneous visualization of images obtained preoperatively with modalities not available during a medical procedure (e.g. high-field MRI), alongside images obtained intraoperatively with modalities not available outside a medical procedure (e.g. optical spectroscopy).

For example, the above methods may allow the generation of a composite image from a preoperative image covering a large area at a relatively low resolution (e.g. MRI phase-contrast), a first intraoperative image covering a subset of the large area at a higher resolution (e.g. Doppler flow ultrasound), and a second intraoperative image covering an even smaller subset of the large area at an even higher resolution (e.g. phase contrast OCT). The composite image thus provides a greater volume of information than any individual image, and can also provide such information at different scales.

Another example advantage is that registering images based on measurements of material properties rather than image features may result in greater registration accuracy, as variances in contrast and colour output between different imaging modalities—which can represent sources of registration error—can be ignored.

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

We claim:

1. A method of image registration, comprising:
   prior to a surgical procedure, obtaining a preoperative image of patient issue at a computing device using a first imaging modality;
   using the first imaging modality, obtaining a first plurality of preoperative measurements of a material property of the patient tissue at the computing device, each measurement of the first plurality of preoperative measurements corresponding to a respective point in the preoperative image;
   storing the preoperative image and the preoperative measurements in a memory of the computing device;
   during the surgical procedure, obtaining an intraoperative image of the patient tissue at the computing device using a second imaging modality;
   using the second imaging modality, obtaining a second plurality of intraoperative measurements of the material property of the patient tissue at the computing device, each measurement of the second plurality of intraoperative measurements corresponding to a respective point in the intraoperative image;
   comparing the first and second pluralities of measurements at the computing device to determine a transformation for registering the preoperative image and the intraoperative image;
   storing the transformation in the memory in association with one of the intraoperative image and the preoperative image;
   applying the transformation to the intraoperative image; and
   controlling a display connected to the computing device to present the preoperative image overlaid with the intraoperative image.

2. The method of claim 1, wherein obtaining the preoperative measurements comprises deriving the preoperative measurements from the preoperative image; and wherein obtaining the intraoperative measurements comprises deriving the intraoperative measurements from the intraoperative image.

3. The method of claim 1, wherein the first imaging modality and the second imaging modality are selected from magnetic resonance imaging (MRI), computed tomography (CT), ultrasound, optical coherence tomography (OCT), and optical spectroscopy.

4. The method of claim 3, wherein one of the first imaging modality and the second imaging modality is OCT, and wherein the corresponding one of the first and second pluralities of measurements are obtained using polarization-sensitive OCT (PS-OCT).

5. The method of claim 3, wherein one of the first imaging modality and the second imaging modality is optical spectroscopy, and wherein the corresponding one of the first and second pluralities of measurements are obtained using Raman spectroscopy.

6. The method of claim 1, wherein the first and second pluralities of measurements of the material property are selected from a list consisting of flow, stiffness, anisotropy, and metabolite concentration.

7. The method of claim 1, wherein the first imaging modality is different from the second imaging modality.

8. The method of claim 1, wherein the preoperative image is registered to the patient tissue; the method further comprising:
   determining a second transformation for registering the intraoperative image to the patient tissue independently of the preoperative image; and determining whether a mismatch exists between the transformation and the second transformation.

9. The method of claim 8, further comprising:
when a mismatch does exist, updating the registration of the preoperative image to the patient tissue.

10. The method of claim 1, further comprising:
retrieving a preoperative model of the material property within the patient tissue;
applying the transformation to the intraoperative image;
comparing the preoperative model with the intraoperative image; and
updating the model from the intraoperative measurements.

11. A computing device, comprising:
a memory;
a display;
a processor interconnected with the memory and the display, the processor configured to:
prior to a surgical procedure, obtain a preoperative image of patient tissue using a first imaging modality;
using the first imaging modality, obtain a first plurality of preoperative measurements of a material property of the patient tissue at the computing device, each measurement of the first plurality of preoperative measurements corresponding to a respective point in the preoperative image;
store the preoperative image and the preoperative measurements in the memory;
during the surgical procedure, obtain an intraoperative image of the patient tissue using a second imaging modality;
using the second imaging modality, obtain a second plurality of intraoperative measurements of the material property of the patient tissue, each measurement of the second plurality of intraoperative measurements corresponding to a respective point in the intraoperative image;
compare the first and second pluralities of measurements to determine a transformation for registering the preoperative image and the intraoperative image;
store the transformation in the memory in association with one of the intraoperative image and the preoperative image;
apply the transformation to the intraoperative image; and
control the display to present the preoperative image overlaid with the intraoperative image.

12. The computing device of claim 11, the processor configured to obtain the preoperative measurements by deriving the preoperative measurements from the preoperative image; and to obtain the intraoperative measurements by deriving the intraoperative measurements from the intraoperative image.

13. The computing device of claim 11, wherein the first imaging modality and the second imaging modality are selected from magnetic resonance imaging (MRI), computed tomography (CT), ultrasound, optical coherence tomography (OCT), and optical spectroscopy.

14. The computing device of claim 13, wherein one of the first imaging modality and the second imaging modality is OCT, and wherein the corresponding one of the first and second pluralities of measurements are obtained using polarization-sensitive OCT (PS-OCT).

15. The method of claim 13, wherein one of the first imaging modality and the second imaging modality is optical spectroscopy, and wherein the corresponding one of the first and second pluralities of measurements are obtained using Raman spectroscopy.

16. The method of claim 11, wherein the first and second pluralities of measurements of the material property are selected from a list consisting of flow, stiffness, anisotropy, and metabolite concentration.

17. The computing device of claim 11, wherein the first imaging modality is different from the second imaging modality.

18. The computing device of claim 11, wherein the preoperative image is registered to the patient tissue; the processor further configured to:
determine a second transformation for registering the intraoperative image to the patient tissue independently of the preoperative image; and
determine whether a mismatch exists between the transformation and the second transformation.

19. The computing device of claim 18, the processor further configured to:
when a mismatch does exist, update the registration of the preoperative image to the patient tissue.

20. The computing device of claim 11, the processor further configured to:
retrieve a preoperative model of the material property within the patient issue from the memory;
apply the transformation to the intraoperative image;
compare the preoperative model with the intraoperative image; and
update the model from the intraoperative measurements.

* * * * *